(12) United States Patent
Nelson et al.

(10) Patent No.: US 8,727,198 B2
(45) Date of Patent: May 20, 2014

(54) SURGICAL STAPLER DELIVERY SYSTEMS AND METHODS OF ASSEMBLING THE STAPLERS

(75) Inventors: Heidi Nelson, Rochester, MN (US); David W Larson, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 270 days.

(21) Appl. No.: 13/254,553

(22) PCT Filed: Mar. 4, 2010

(86) PCT No.: PCT/US2010/026220
§ 371 (c)(1),
(2), (4) Date: Sep. 2, 2011

(87) PCT Pub. No.: WO2010/102115
PCT Pub. Date: Sep. 10, 2010

(65) Prior Publication Data
US 2011/0315741 A1     Dec. 29, 2011

Related U.S. Application Data

(60) Provisional application No. 61/157,792, filed on Mar. 5, 2009.

(51) Int. Cl.
*A61B 17/068* (2006.01)

(52) U.S. Cl.
USPC .................................. 227/176.1; 227/175.1

(58) Field of Classification Search
USPC ......... 227/176.1, 175.1, 180.1; 606/153, 139; 128/898
See application file for complete search history.

(56) References Cited

U.S. PATENT DOCUMENTS

| | | | |
|---|---|---|---|
| 5,411,508 A * | 5/1995 | Bessler et al. ................ | 606/153 |
| 6,343,731 B1 | 2/2002 | Adams et al. | |
| 7,020,531 B1 * | 3/2006 | Colliou et al. ................ | 607/133 |
| 2001/0056282 A1 | 12/2001 | Sonnenschein et al. | |
| 2007/0219571 A1 * | 9/2007 | Balbierz et al. ............... | 606/153 |
| 2007/0282356 A1 * | 12/2007 | Sonnenschein et al. ...... | 606/153 |
| 2008/0190991 A1 | 8/2008 | Milliman | |
| 2008/0208213 A1 | 8/2008 | Benjamin et al. | |

FOREIGN PATENT DOCUMENTS

WO     2007/141776 A2     12/2007

OTHER PUBLICATIONS

Official Communication issued in International Patent Application No. PCT/US2010/026220, mailed on Oct. 8, 2010.

* cited by examiner

*Primary Examiner* — Thanh Truong
*Assistant Examiner* — Nathaniel Chukwurah
(74) *Attorney, Agent, or Firm* — Keating & Bennett, LLP

(57) ABSTRACT

Surgical stapler delivery systems and methods of using the delivery systems to deliver and assemble surgical staplers are described herein.

24 Claims, 10 Drawing Sheets

SURGICAL STAPLER DELIVERY SYSTEMS AND METHODS OF ASSEMBLING THE STAPLERS

RELATED APPLICATION

The present application claims the benefit under 35 U.S.C. §119(e) of U.S. Provisional Patent Application No. 61/157,792, filed on Mar. 5, 2009 and titled SURGICAL STAPLER DELIVERY SYSTEMS AND METHODS OF ASSEMBLING THE STAPLERS, which is hereby incorporated by reference in its entirety.

Surgical stapler delivery systems and methods of assembling surgical staplers are described herein.

The use of conventional surgical staplers in many procedures can be problematic due to the size of the staplers. These size constraints may be especially problematic when the surgical staplers are to be used in laparoscopic procedures in the pelvic region.

SUMMARY

Surgical stapler delivery systems and methods of using the delivery systems to deliver and assemble surgical staplers are described herein.

The surgical staplers may be useful in the stapling of tissue in the pelvic region, e.g., for the stapling of the colon or rectum, mesentery for the purpose of surgical resection of neoplasia (polyps, cancer, etc.), or for other conditions, etc.

The staplers and methods described herein may be used in, e.g., laparoscopic, endoscopic, intra-luminal or NOTES procedures, as well as in open surgical procedures.

In some embodiments, the staplers may include components that are delivered over a guidewire to a selected location where they are assembled into a functional stapling device that can be operated and, if desired, potentially disassembled for removal.

In one aspect, a stapler delivery system is provided that includes a backstop having a backstop lumen extending through the backstop, the backstop lumen extending between a first opening and a second opening; an anvil having a distal end operably connectable to the backstop; a staple cartridge having a distal end operably connectable to the backstop such that a working surface of the anvil faces a working surface of the staple cartridge; wherein the staple cartridge includes a plurality of staples and, optionally, an actuating bead, wherein the staple cartridge optionally includes a cutting element; wherein the anvil and the staple cartridge (and optionally the backstop) are located within one or more delivery sheaths in a disassembled configuration.

In some embodiments of the systems described herein, the system further includes a guidewire threaded through at least one of the anvil and the staple cartridge while the anvil and the staple cartridge are located within the one or more delivery sheaths in the disassembled configuration.

In some embodiments of the systems described herein, the anvil, the backstop, and the staple cartridge are located within a single delivery sheath in the disassembled configuration.

In some embodiments of the systems described herein, the backstop is located in a first delivery sheath and the anvil and the staple cartridge are located in a second delivery sheath when the backstop, the anvil, and the staple cartridge are in the disassembled configuration.

In some embodiments of the systems described herein, the backstop includes a tissue restriction element that spans a gap between the staple cartridge and the anvil when the staple cartridge and the anvil are connected to the backstop. In some embodiments, the tissue restriction element is pivotally connected to the backstop such that the tissue restriction element rotates about an axis that extends through the backstop. In some embodiments, the tissue restriction element includes a flexible component that extends between a first end and a second end of the backstop, wherein the flexible component is held under tension between the first end and the second end.

In some embodiments of the systems described herein, the system includes an end cap configured for attachment to the staple cartridge and the anvil.

In another aspect, a stapler delivery system is provided that includes an anvil having a hinged end and a free end; a staple cartridge having a hinged end and a free end; a hinged backstop rotatably connected to the hinged ends of the staple cartridge and the anvil, wherein, during advancement of the anvil, the staple cartridge and the hinged backstop through a channel in a delivery sheath, the hinged backstop is located between the anvil and the staple cartridge; wherein rotation of the anvil and/or the staple cartridge about the hinged backstop places a working surface of the anvil facing a working surface of the staple cartridge.

In some embodiments of the systems described herein, the hinged backstop defines a first and a second axis of rotation that are spaced apart from each other, and wherein the anvil rotates about the first axis of rotation and the stapler cartridge rotates about the second axis of rotation.

In some embodiments of the systems described herein, the anvil, the hinged backstop, and the staple cartridge are located within a delivery sheath in a disassembled configuration.

In another aspect, a method of assembling a stapler is provided that includes providing a delivery sheath having a proximal end and a distal end; locating a backstop and the distal end of the delivery sheath proximate each other, the backstop having a backstop lumen extending through the backstop, the backstop lumen extending between a first opening and a second opening; advancing a first end of a guidewire through the delivery sheath towards the distal end of the delivery sheath; directing the first end of the guidewire through the delivery sheath and into the first opening of the backstop lumen followed by advancing the first end of the guidewire through the backstop lumen until the first end of the guidewire exits the backstop lumen through the second opening; directing the first end of the guidewire back into the delivery sheath after the first end exits the second opening of the backstop lumen, following by advancing the first end of the guidewire towards the proximal end of the delivery sheath; advancing an anvil through the delivery sheath towards the distal end of the delivery sheath, wherein advancing the anvil through the delivery sheath includes advancing the anvil over at least a portion of the guidewire until the anvil exits the delivery sheath proximate the distal end of the delivery sheath; operably connecting a distal end of the anvil to the backstop after the anvil has exited from the delivery sheath; advancing a staple cartridge through the delivery sheath towards the distal end of the delivery sheath, wherein advancing the staple cartridge through the delivery sheath includes advancing the staple cartridge over at least a portion of the guidewire until the staple cartridge exits the delivery sheath proximate the distal end of the delivery sheath, wherein the staple cartridge includes a plurality of staples and an actuating bead, wherein the staple cartridge optionally includes a cutting element; operably connecting a distal end of the staple cartridge to the backstop after the staple cartridge has exited from the delivery sheath, wherein the staple cartridge opposes the anvil; operably connecting a proximal end of the anvil to a proximal end of the staple cartridge; optionally driving a plurality of staples of the plurality of staples from the staple cartridge against the anvil after operably connecting the proximal end of the anvil to a proximal end of the staple cartridge.

In some embodiments, the delivery sheath may include a delivery lumen that includes a proximal opening proximate the proximal end of the delivery sheath and a distal opening proximate the distal end of the delivery sheath, and locating the backstop and the distal end of the delivery sheath proximate each other includes advancing the backstop through the delivery lumen until the backstop exits the delivery lumen from the distal opening.

In some embodiments, the delivery sheath may include a first guidewire lumen, and directing the first end of the guidewire through the delivery sheath and into the first opening of the backstop lumen includes advancing the first end of the guidewire through the first guidewire lumen. In some embodiments, the delivery sheath may also include a second guidewire lumen, and directing the first end of the guidewire back into the delivery sheath after the first end exits the second opening of the backstop lumen and advancing the first end of the guidewire towards the proximal end of the delivery sheath includes advancing the first end of the guidewire through the second guidewire lumen.

In some embodiments, operably connecting a proximal end of the anvil to a proximal end of the staple cartridge may include operably connecting an end cap to the proximal ends of the staple cartridge and the anvil. If used, the end cap may be delivered to a location proximate the staple cartridge and the anvil through the delivery sheath. In some embodiments, the guidewire may be threaded through at least one opening in the end cap.

In another aspect, a method of assembling a stapler may be provided that includes advancing hinged stapler components through a delivery sheath towards a distal end of the delivery sheath, wherein the stapler components include an anvil having a hinged end and a free end and a staple cartridge having a hinged end and a free end, wherein the hinged ends of the staple cartridge and the anvil are rotatably connected to each other through a hinged backstop, wherein the anvil and the staple cartridge are advanced through the delivery sheath in series with each other such that the hinged backstop is located between the anvil and the staple cartridge, and wherein the anvil and the staple cartridge exit the delivery sheath proximate the distal end of the delivery sheath; rotating the anvil and/or the staple cartridge about the hinged backstop after the anvil and the staple cartridge exit the delivery sheath such that a working surface of the anvil faces a working surface of the staple cartridge; and operably connecting the free end of the anvil to the free end of the staple cartridge.

In some methods, the hinged backstop defines a first and a second axis of rotation that are spaced apart from each other, and the anvil rotates about the first axis of rotation and the stapler cartridge rotates about the second axis of rotation.

In some methods, advancing the hinged stapler components may include advancing the hinged stapler components over a guidewire.

In some methods, the delivery sheath includes a delivery lumen that has a proximal opening proximate the proximal end of the delivery sheath and a distal opening proximate the distal end of the delivery sheath, and advancing hinged stapler components includes advancing the hinged stapler components through the delivery lumen until both the anvil and the stapler cartridge exit the delivery lumen from the distal opening.

In some methods, operably connecting the free end of the anvil to the free end of the staple cartridge includes operably connecting an end cap to the proximal ends of the staple cartridge and the anvil. If used, the end cap may be delivered to a location proximate the staple cartridge and the anvil through the delivery sheath.

Some methods as described herein may include optionally driving a plurality of staples of the plurality of staples from the staple cartridge against the anvil after operably connecting the free end of the anvil to the free end of the staple cartridge. Such a connection may optionally be made through both a backstop and an end cap.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, an anvil may be used to refer to one, two, or more anvils.

The term "and/or" means one or all of the listed elements or a combination of any two or more of the listed elements.

The above summary is not intended to describe each embodiment or every implementation of the surgical staplers and methods of use. Rather, a more complete understanding of the surgical staplers and methods of use will become apparent and appreciated by reference to the following Description of Illustrative Embodiments and claims in view of the accompanying figures of the drawing.

BRIEF DESCRIPTION OF THE VIEWS OF THE DRAWING

The surgical staplers and methods of use will be further described with reference to the views of the drawing, wherein.

DESCRIPTION OF ILLUSTRATIVE EMBODIMENTS

In the following description of illustrative embodiments, reference is made to the accompanying figures of the drawing which form a part hereof, and in which are shown, by way of illustration, specific embodiments of surgical staplers and methods of assembling and/or using the same. It is to be understood that other embodiments may be utilized and structural changes may be made without departing from the scope of the present invention.

Figure 1:
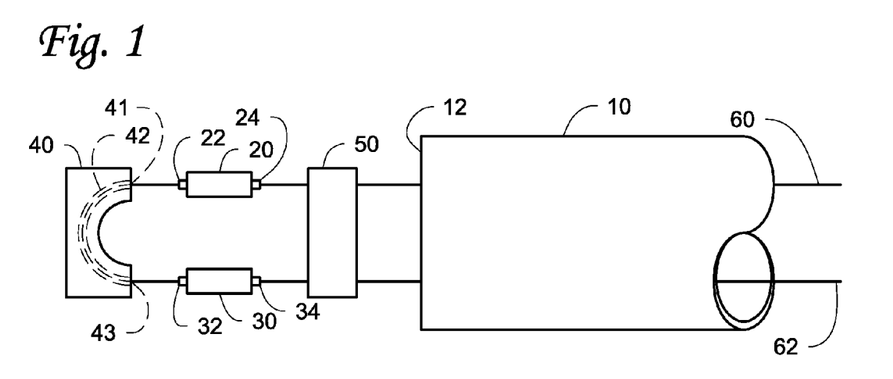
FIG. 1 depicts one embodiment of a surgical stapler delivery system.

One embodiment of a surgical stapler delivery system is depicted in FIG. 1 and its construction and use/assembly will be described herein. The system includes a delivery sheath 10 through which all or some of the stapler components may be delivered. The distal end 12 of the sheath 10 is depicted in FIG. 1, with the proximal end not seen in FIG. 1. The delivery sheath 10 may be in the form of an endoscope, laparoscope, introducer, etc.—essentially any elongated body that can include one or more lumens with openings proximate the proximal and distal ends of the delivery sheath.

The stapler depicted in FIG. 1 includes an anvil 20, staple cartridge 30 and backstop 40. The stapler of FIG. 1 also includes an optional end cap 50. The stapler components may preferably be assembled proximate the end of the delivery sheath or the delivery sheath may be withdrawn after any components delivered therethrough have been delivered to a selected location.

The assembly may begin, e.g., by locating a backstop 40 and the distal end 12 of the delivery sheath 10 proximate each other. The backstop 40 may preferably include a backstop lumen 42 that extends through the backstop 40. The backstop lumen 42 may, for example, extending between a first opening 41 and a second opening 43. Although depicted and described as a closed lumen, the backstop lumen may alternatively be an open channel or other structure that can retain an operable connection between the guidewire and the backstop to facilitate assembly of the staplers.

The method may also involve advancing a first end 62 of a guidewire 60 through the delivery sheath 10 towards the distal end 12 of the delivery sheath 10, followed by directing the first end 62 of the guidewire 60 through the delivery sheath 10 and into the first opening 41 of the backstop lumen 42 followed by advancing the first end 62 of the guidewire 60 through the backstop lumen 42 until the first end 62 of the guidewire 60 exits the backstop lumen 42 through the second opening 43.

The first end 62 of the guidewire 60 is then directed back into the delivery sheath 10 after the first end 62 exits the second opening 43 of the backstop lumen 42, following by advancing the first end of the guidewire 60 towards the proximal end of the delivery sheath 10.

The method also includes advancing an anvil 20 through the delivery sheath 10 towards the distal end 12 of the delivery sheath, wherein advancing the anvil 20 through the delivery sheath 10 comprises advancing the anvil over at least a portion of the guidewire 60 until the anvil 20 exits the delivery sheath 10 proximate the distal end 12 of the delivery sheath. The distal end 22 of the anvil 20 can be operatively connected to the backstop 40 after the anvil 20 has exited from the delivery sheath 10.

The method further includes advancing a staple cartridge 30 through the delivery sheath 10 towards the distal end 12 of the delivery sheath, wherein advancing the staple cartridge 30 through the delivery sheath 10 includes advancing the staple cartridge 30 over at least a portion of the guidewire 60 until the staple cartridge 30 exits the delivery sheath 10 proximate the distal end 12 of the delivery sheath 10.

The staple cartridge 30 preferably includes a plurality of staples and an actuating bead and may also include a cutting element (e.g., a blade, etc.). The distal end 32 of the staple cartridge 30 may preferably be operably connected to the backstop 40 after the staple cartridge 30 has exited from the delivery sheath 10. It may be preferred that the staple cartridge 30 be advanced over the guidewire 60 such that the staple cartridge 30 is located opposite from the anvil 20.

The proximal end 24 of the anvil 20 is operably connected to the proximal end 34 of the staple cartridge 30 such that the assembled stapler, when operated, can staple and, optionally, cut tissue located between the anvil 20 and the staple cartridge 30. For example, the method may include optionally driving a plurality of staples of the plurality of staples from the staple cartridge 30 against the anvil 20 after operably connecting the proximal end 24 of the anvil 20 to a proximal end 34 of the staple cartridge 30.

In various embodiments, the delivery sheath 10 may include a delivery lumen that includes a proximal opening proximate the proximal end of the delivery sheath and a distal opening proximate the distal end 12 of the delivery sheath 10. In the methods, locating the backstop 40 and the distal end 12 of the delivery sheath 10 proximate each may include advancing the backstop 40 through the delivery lumen until the backstop exits the delivery lumen from the distal opening.

In some embodiments, the delivery sheath 10 may include a first guidewire lumen, and directing the first end 62 of the guidewire 60 through the delivery sheath 10 and into the first opening 41 of the backstop lumen 42 may include advancing the first end of the guidewire through the first guidewire lumen in the delivery sheath 10.

In some embodiments, the delivery sheath 10 may include a second guidewire lumen, and directing the first end 62 of the guidewire 60 back into the delivery sheath 10 after the first end 62 exits the second opening 43 of the backstop lumen 42 and advancing the first end of the guidewire towards the proximal end of the delivery sheath 10 may include advancing the first end 62 of the guidewire 60 through the second guidewire lumen in the delivery sheath 10.

In some embodiments, operably connecting the proximal end 24 of the anvil 20 to the proximal end 34 of the staple cartridge 30 may include operably connecting an end cap 50 to the proximal ends 24, 34 of the anvil 20 and the staple cartridge 30. The end cap 50 may preferably be delivered to a location proximate the staple cartridge 30 and the anvil 20 through the delivery sheath 10. The guidewire 60 may be threaded through at least one opening in the end cap 50 in some embodiments.

One illustrative method of assembling a surgical stapler similar to that depicted in FIG. 1 is depicted in the series of FIGS. 2-6. The stapler components in the depicted method are deployed through two delivery sheaths 10A and 10B. In the depicted system, a backstop 40 is deployed through delivery sheath 10A while the remainder of the components are preferably deployed through delivery sheath 10B. Delivery of all of the components may, in some embodiments, be carried out using only one delivery sheath. The stapler components are delivered, in the depicted figures, to the pelvic region proximate the colon 2, although surgical staplers such as those described herein may be assembled in other areas and/or for other procedures.

Figure 2:
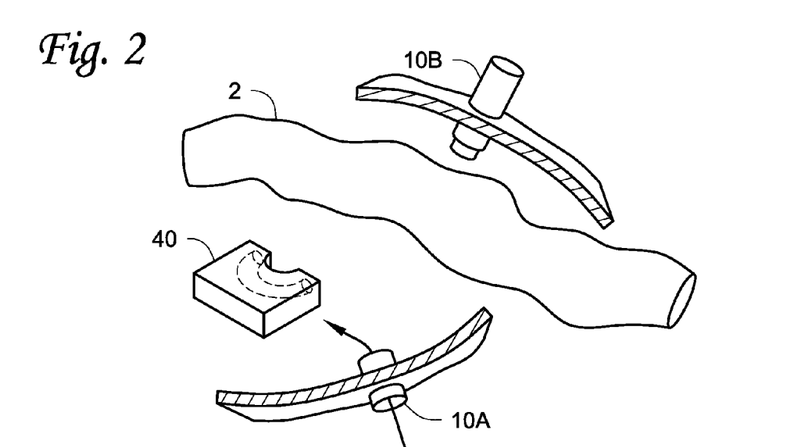
FIGS. 2-6 depicts one method of delivering and assembling the surgical stapler of FIG. 1.

As depicted in FIG. 2, the backstop 40 is deployed through delivery sheath 10A. It may advantageously be located on one side of the colon 2 within the pelvic region.

Figure 3:
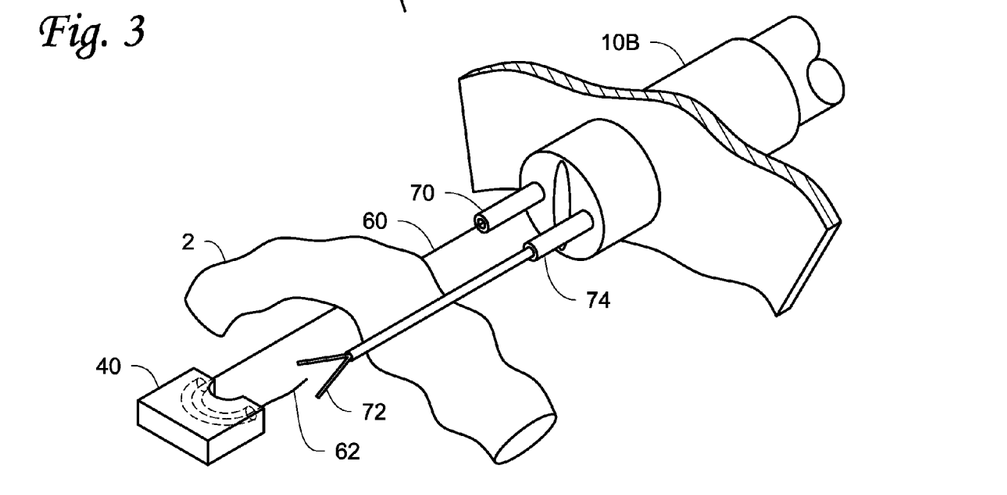

Referring to FIG. 3, a guidewire 60 is deployed through a first lumen 70 that extends through the delivery sheath 10B. The guidewire 60 is preferably directed into and through a backstop lumen provided in the backstop 40. After passing through the backstop 40, the tip 62 of the guidewire 60 may be grasped by a grasping tool 72 and drawn proximally into a second lumen 74 that also extends through the delivery sheath 10.

The tip of the guidewire 60 is drawn or advanced proximally through the delivery sheath 10B towards the proximal end of the delivery sheath and, as a result, a first portion of the guidewire 60 extends through the first lumen 70 of the delivery sheath 10B and a second portion of the guidewire 60 extends through the second lumen 74 of the delivery sheath 10B. In the depicted embodiment, the guidewire 60 includes a third portion that extends from the distal end of the first lumen 70 to the distal end of the second lumen 74, with the third portion passing through the backstop 40. It may be preferred that the third portion of the guidewire 60 passes around the colon 2 as seen in, e.g., FIG. 4.

Figure 4:
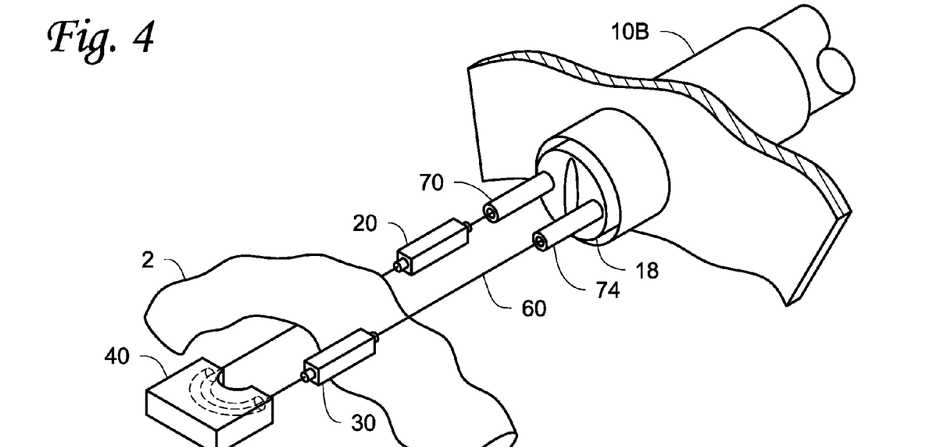

Referring to, e.g., FIG. 4, the first portion of the guidewire 60 that is located within the delivery sheath 10 is then preferably threaded through or can otherwise serve as a guide for an anvil 20 which is delivered through the delivery sheath 10 by passing the anvil through the first lumen 70. Similarly, the second portion of the guidewire 60 that is located within the delivery sheath 10 is also preferably threaded through or can otherwise serve as a guide for a staple cartridge 30 which is delivered through the delivery sheath 10 by passing the staple cartridge 30 through the second lumen 74.

Figure 5:
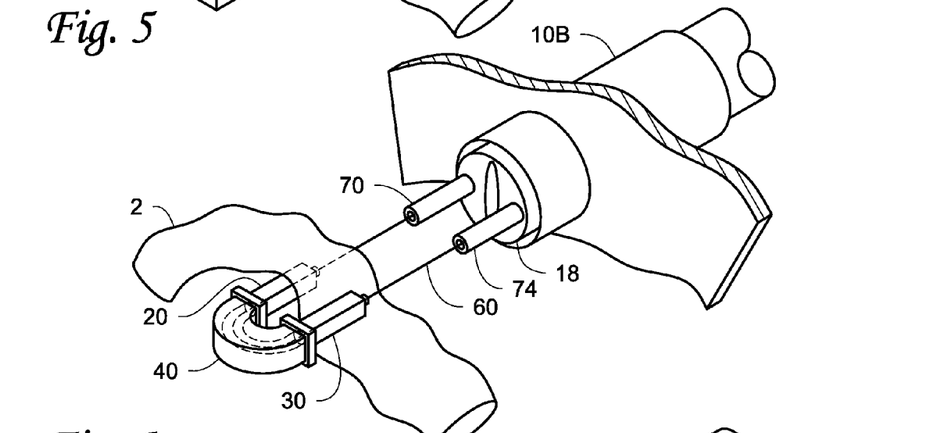

Turning to FIG. 5, the anvil 20 and the staple cartridge 30 are preferably operably connected to the backstop 40 as described herein such that working surfaces of both the anvil 20 and the staple cartridge 30 face each other.

Figure 6:
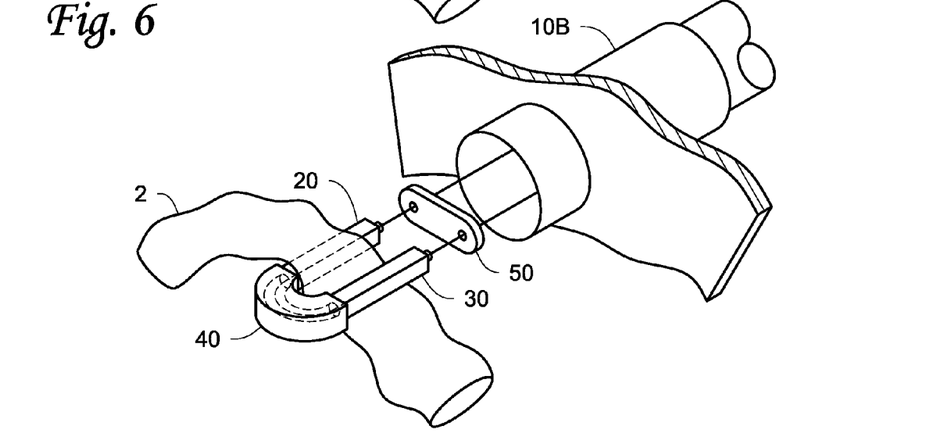

With the anvil 20 and the staple cartridge 30 connected to the backstop 40, an end cap 50 may be advanced through the delivery sheath and operably attached to the proximal ends of the anvil 20 and the staple cartridge 30 as depicted in, e.g., FIG. 6.

Figure 7:
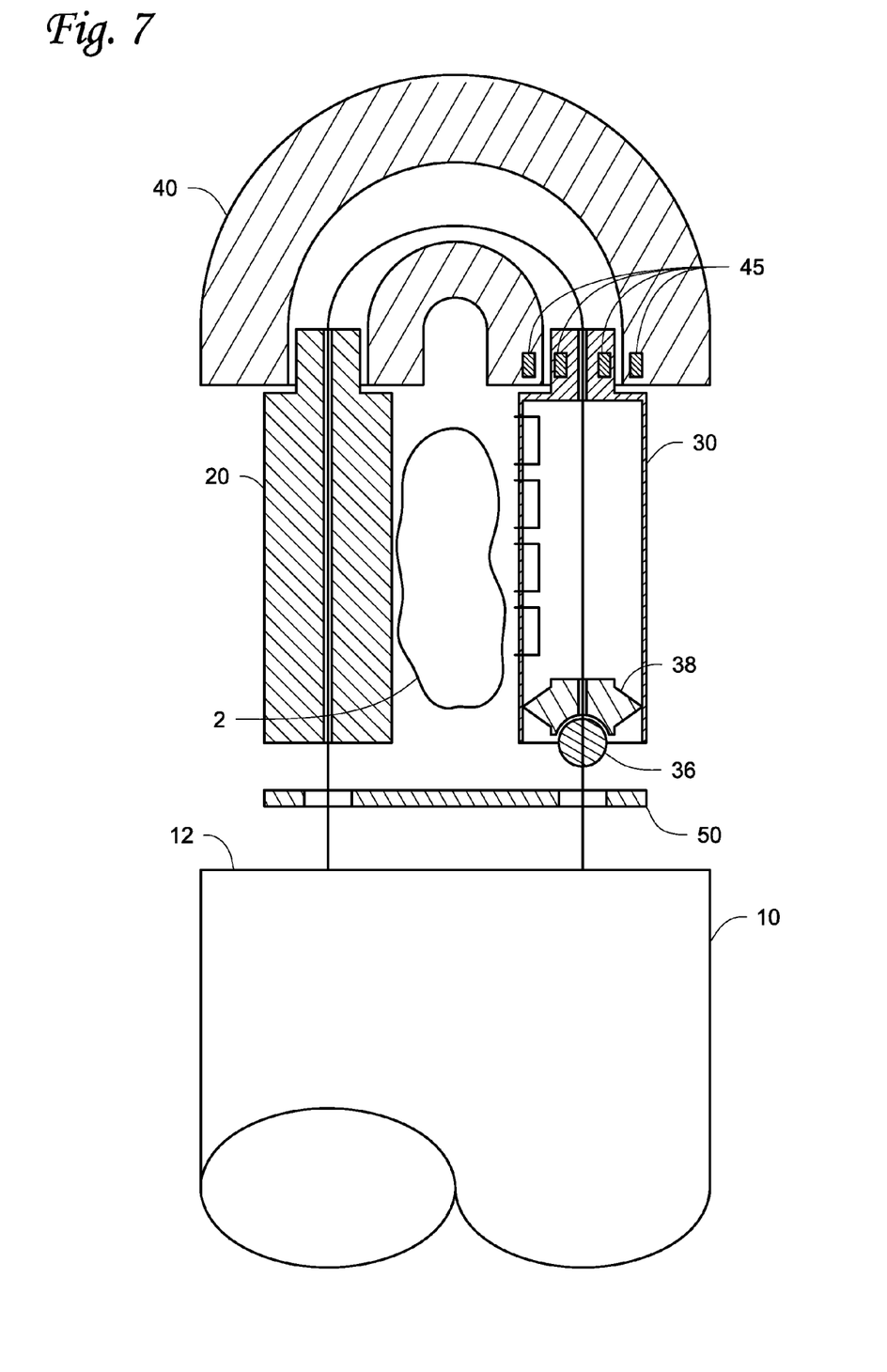
FIG. 7 is a view of a surgical stapler.

FIG. 7 is an enlarged view of an assembled stapler that includes an anvil 20, staple cartridge 30, backstop 40 and end cap 50, all of which are located proximate the distal end 12 of a delivery sheath 10. Some other features depicted in FIG. 7 include the use of magnets 45 or other position sensing structures that may be used to assist with assembly of the anvil 20 and/or staple cartridge 30. In the case of magnets, the magnets 45 in the different components may attract each other to assist in alignment of the components. The ends of the different components may also include complementary shapes, e.g., be keyed, etc. to assist in assembly of the stapler components.

Other optional components that may be included in various embodiments of the staplers described herein may include an actuation mechanism for driving the staples from the staple cartridge 30 against the anvil 20 to staple tissue 2 located between the anvil 20 and the staple cartridge 30. The actuation mechanism may be in any suitable form. In the depicted embodiment, the actuation mechanism is in the form of a wedge/bead/etc. 36 that can be driven through the staple cartridge 30 to drive the staples towards the anvil 20. Examples of some potentially suitable stapler actuation mechanisms may be described in, e.g., U.S. Pat. No. 6,698,643 to Whitman and the documents referenced therein.

Another optional component depicted in connection with the stapler of FIG. 7 is a blade 38 that may be used to cut tissue located between the staple cartridge 30 and the anvil 20. The blade 38 may take many different forms and more than one blade may be provided. Various constructions of staplers incorporating blades or other cutting devices will be known to those skilled in the art and will not be described in detail herein.

Another optional feature of staplers described herein that may be described in connection with FIGS. 4-5 is that the delivery sheath 10 may include an inner sheath 18 within the outer delivery sheath 10. The inner sheath 18 may include separate lumens for delivering the various components of the stapler as described above and, after delivery of the components and/or their assembly into a stapler, the inner sheath 18 may be removed to provide a larger lumen in the delivery sheath 10 that may facilitate operation of the stapler, delivery of other instruments, removal of the assembled stapler without requiring disassembly of the stapler, etc. For example, rotation of the inner sheath 18 may be allowed such that, e.g., the stapler components being delivered can be oriented to facilitate assembly of the stapler about selected structure (e.g., tissue).

Figure 8:
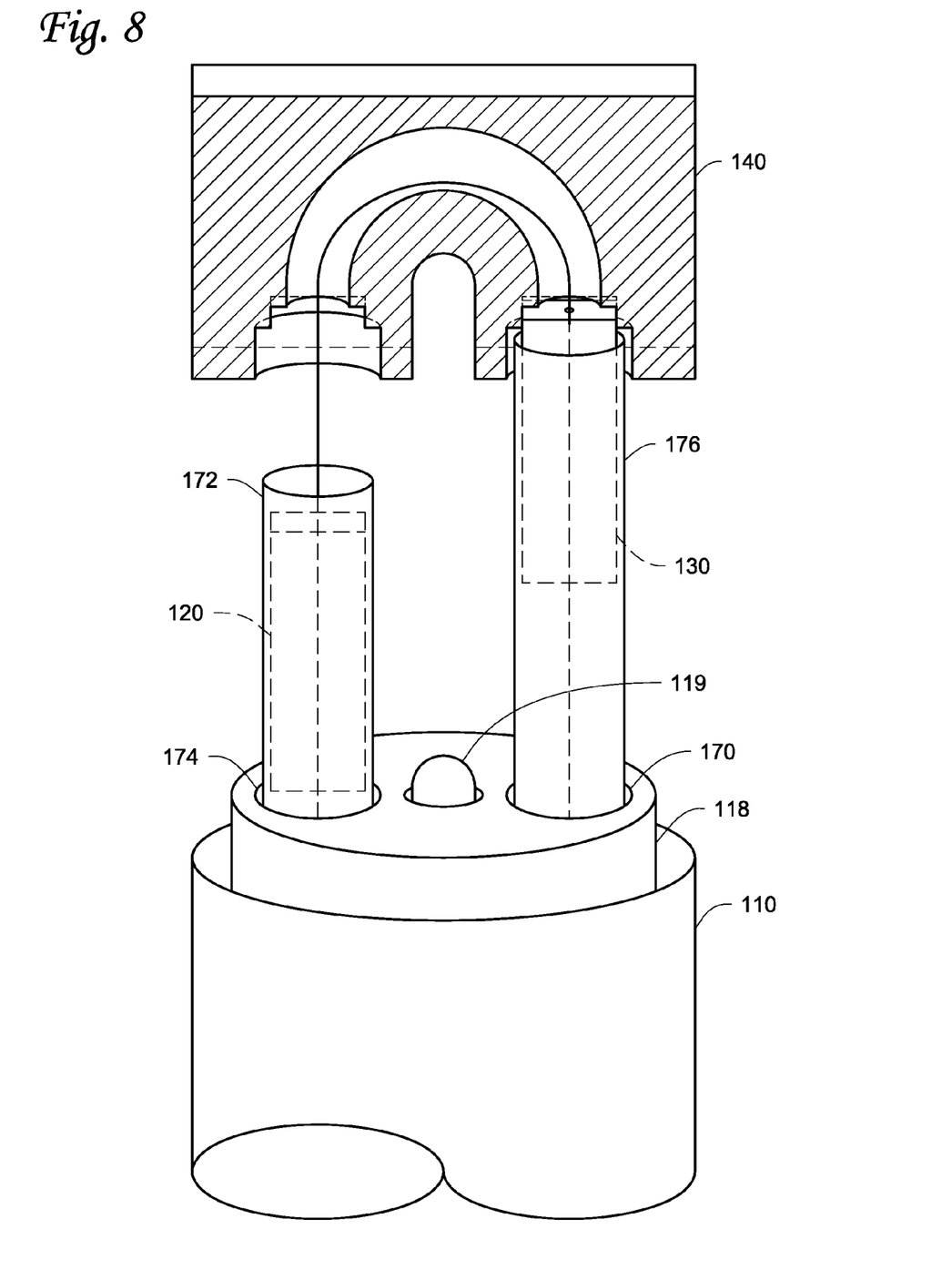
FIG. 8 is another surgical stapler delivery system.

Another embodiment of a surgical stapler and delivery system is depicted in connection with FIG. 8. Like the embodiments described above, the stapler may include an anvil 120, staple cartridge 130, and backstop 140. The system of FIG. 8 also includes an outer delivery sheath 110 and inner sheath 118. The inner sheath may preferably include multiple lumens 170 and 174. Component sheaths 172 and 176 may be delivered through the lumens. In turn, the component sheaths (which may be advanced distally and/or retracted proximally within the lumens) may be used to deliver a guidewire and/or anvil 120 and staple cartridge 130. The inner sheath 118 may also include additional components such as, e.g., an imaging device 119 to assist a user in monitoring the stapler assembly process.

Figure 9:
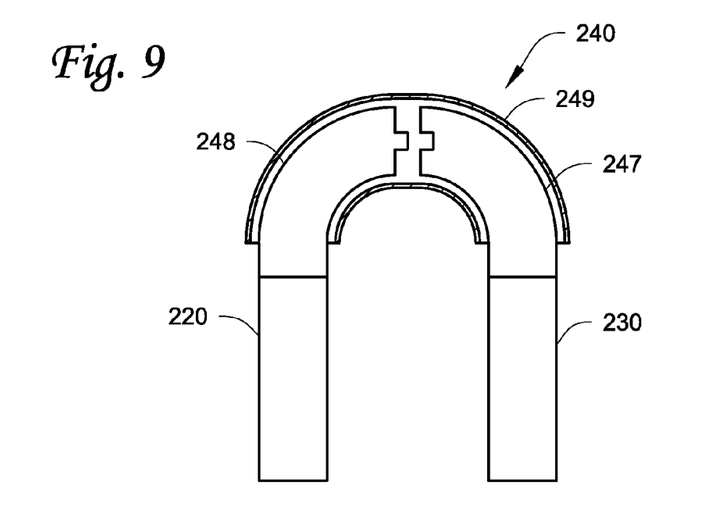
FIG. 9 depicts a two-piece backstop for a surgical stapler.

Still other variations are depicted in connection with FIG. 9 in which a multi-piece backstop 240 is provided. The backstop 240 may be assembled using two different components 247 and 248. The components 247 and 248 may form equal portions of the completed backstop 240, but that is not necessary. The components 247 and 248 may include features designed to assist with the connection process such as complementary keyed ends, magnets, proximity sensors, etc. A backstop sheath 249 may be provided over the assembled components 247 and 248 to assist in aligning and/or securing the components to each other. In such an embodiment, the backstop components 247 and 248 may be provided as integral components of the anvil 220 and staple cartridge 230 or they may be provided as separate and discrete articles that are attached or connected to the anvil 220 and staple cartridge 230.

Figure 10:
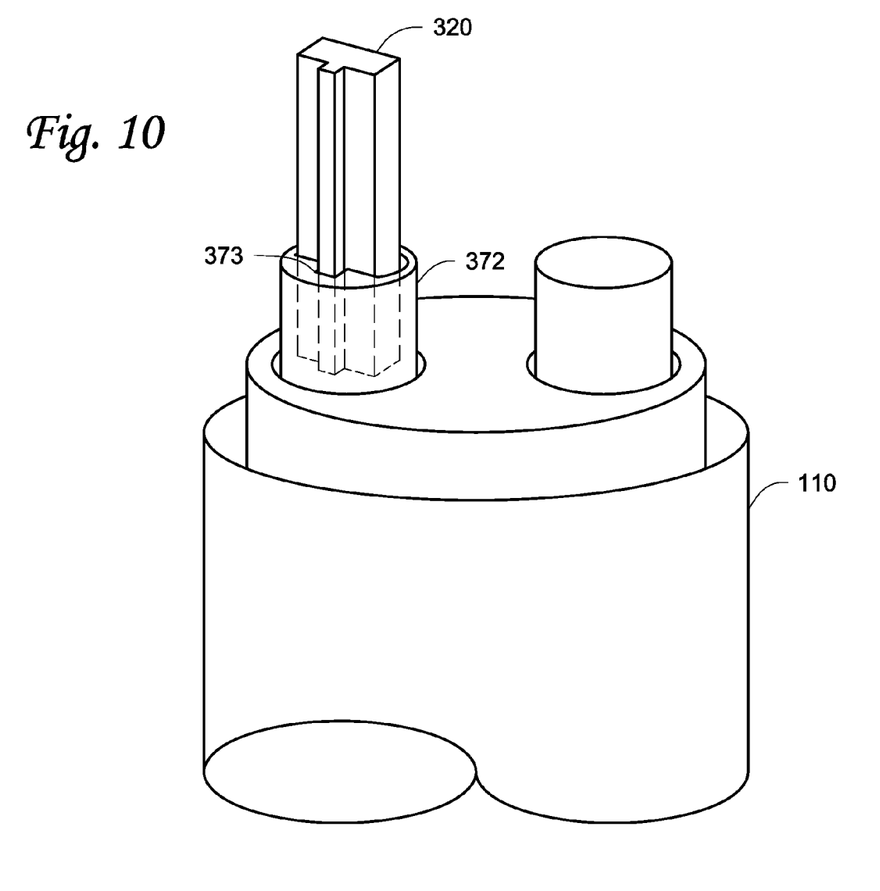
FIG. 10 depicts another variation in a delivery system including an inner sheath for aligning components.

FIG. 10 depicts another variation in which a component sheath 372 may include an alignment notch 373 that cooperates with corresponding structure on an anvil 320 to assist in aligning the anvil with other stapler components during the assembly process. Similar structures may be used in connection with the staple cartridge to facilitate its alignment as well. By connecting the component with its component sheath, rotation of the proximal end of the component sheath 372 may preferably result in corresponding rotation of the component being delivered therethrough.

Figure 11:
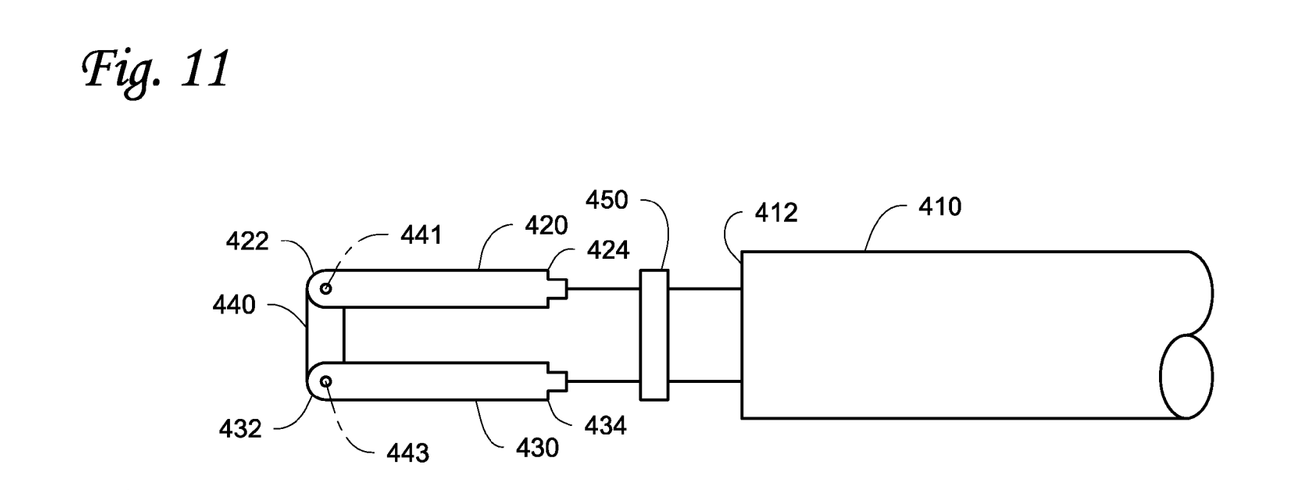
FIG. 11 depicts an embodiment of a hinged surgical stapler delivery system.
Figure 12:
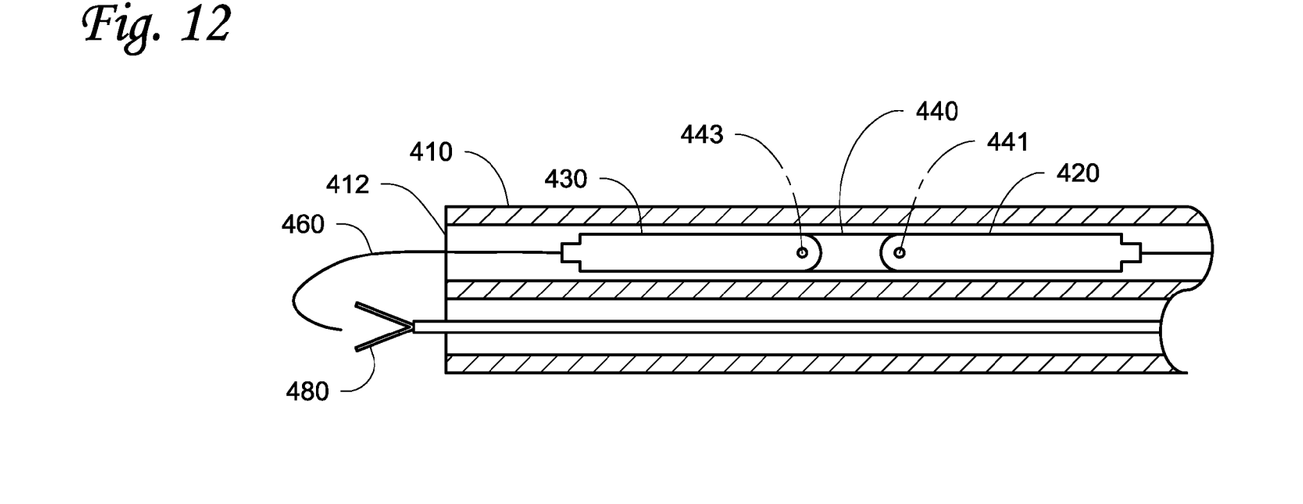
FIG. 12 depicts the hinged stapler of FIG. 11 in a delivery sheath.

FIGS. 11 and 12 depict another embodiment of a surgical stapler in the form of a hinged stapler, with the hinged stapler including an anvil 420, staple cartridge 430. In the depicted embodiment, the anvil 420 is operably connected to the staple cartridge 430 through a hinged backstop 440. The anvil 420 includes a hinged end 422 and a free end 424 and the staple cartridge 430 also includes a hinged end 432 and a free end 434. The hinged ends 422, 424 of the anvil 420 and the staple cartridge 430 are rotatably connected to each other through the hinged backstop 440. In use, the anvil 420 and the staple cartridge 430 are advanced through the delivery sheath 410 in series with each other such that the hinged backstop 440 is located between the anvil 420 and the staple cartridge 430 (see, e.g., FIG. 12) until the anvil 420 and the staple cartridge 430 exit the delivery sheath 410 proximate the distal end 412 of the delivery sheath 410.

After the components have exited the delivery sheath 410, the anvil 420, staple cartridge 430 and hinged backstop 440 may preferably rotate relative to each other such that a working surface of the anvil 420 faces a working surface of the staple cartridge 430.

With the components in position, the assembly process may include operably connecting the free end 424 of the anvil 420 to the free end 434 of the staple cartridge 430. That connection may optionally be made using an end cap 450 as discussed above in connection with the stapler of FIG. 1. Also, although not depicted, the end cap 450 could optionally be rotatably or hingedly connected to the anvil 420 or the staple cartridge 430 in some embodiments.

In some embodiments, the hinged stapler components may be delivered over a guidewire 460 as depicted in FIG. 12, with the free end of the guidewire being captured by, e.g., a grasping element 480 as discussed above in connection with FIG. 3.

As seen in FIGS. 11 and 12, the hinged backstop 440 may defines a first axis of rotation 441 and a second axis of rotation 443 that are spaced apart from each other across the hinged backstop 440, with the anvil 420 rotating about the first axis of rotation 441 and the staple cartridge 430 rotating about the second axis of rotation 443 during the assembly process. In other embodiments, however, the anvil and the staple cartridge may potentially be connected directly to each other and rotate about a single common axis of rotation.

Figure 13:
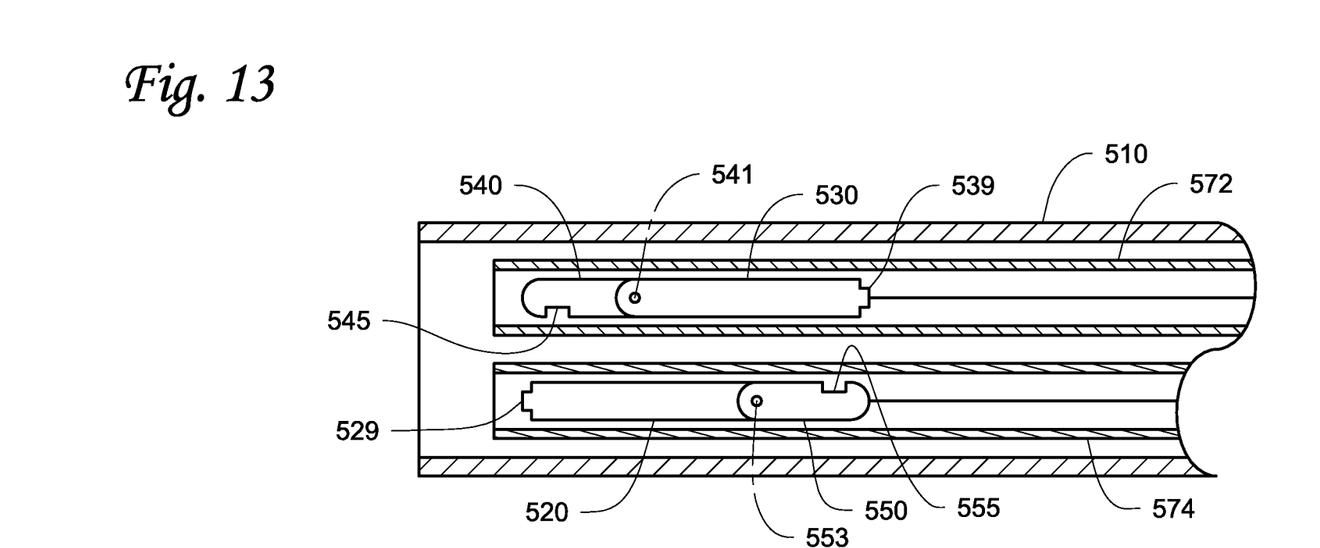
FIG. 13 depicts another embodiment of a hinged surgical stapler delivery system.
Figure 14:
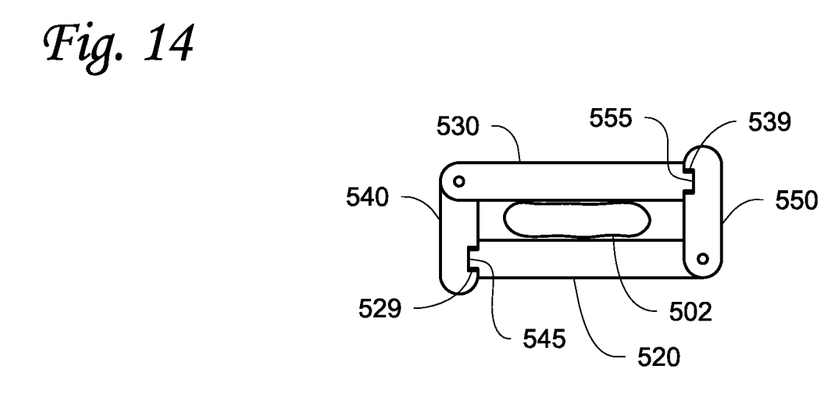
FIG. 14 depicts the stapler of FIG. 13 after assembly.

One potential method of assembling a stapler proximate the distal end of a delivery sheath is depicted in connection with FIGS. 13-14. The stapler components are depicted as being delivered through a delivery sheath 510 and rotated into position about, e.g., selected structure 502 (FIG. 14).

The stapler components include an anvil 520 and a staple cartridge 530, as well as a hinged backstop 540 and a hinged end cap 550. In this depicted embodiment, the staple cartridge 530 is hingedly connected to the hinged backstop 540 for rotation about axis of rotation 541. The staple cartridge 530 and hinged backstop 540 are delivered through the delivery sheath 510 using a component sheath 572. The anvil 520 of this embodiment is hingedly connected to a hinged end cap 550 for rotation about axis of rotation 553. The anvil 520 and hinged end cap 550 are delivered through the delivery sheath 510 using a component sheath 574. The component sheaths 572 and 574 are located within a common channel/lumen in the delivery sheath 510, although separate channels/lumens may alternatively be used.

As a part of the assembly process, the staple cartridge 530 and attached hinged backstop are ejected or otherwise removed from the component sheath 572 and rotated relative to each other about, e.g., axis of rotation 541. The anvil 520 and attached hinged end cap 550 are also ejected or otherwise removed from component sheath 574 and may be rotated relative to each other about, e.g., axis of rotation 553.

The hinged backstop 540 and the distal end of the anvil 520 may preferably include alignment/attachment features that facilitate alignment and operable attachment of the anvil 520 to the hinged backstop 540. In the depicted embodiment, those alignment/attachment features may take the form of a slot 545 and pin 529, although many other variations are possible.

Similarly, the hinged end cap 550 and the proximal end of the staple cartridge 530 may preferably include alignment/attachment features that facilitate alignment and operable attachment of the staple cartridge 530 to the hinged end cap 550. In the depicted embodiment, those alignment/attachment features may take the form of a slot 555 and pin 539, although many other variations are possible.

The assembled stapler is depicted in FIG. 14, with a selected structure (e.g., colon, other tissue, etc.) located between the anvil 520 and the staple cartridge 530 which are operably connected to each other through backstop 540 and end cap 550.

Among potential variations of this embodiment, the end cap 550 may be provided separately from the anvil 520 (as in, e.g., the embodiments described above), with the backstop 540 and staple cartridge 530 being hinged together as depicted in FIGS. 13 and 14. Further, the anvil 520 and staple cartridge 530 may be delivered using separate and distinct delivery sheaths. Many other variations are possible.

Figure 15A:
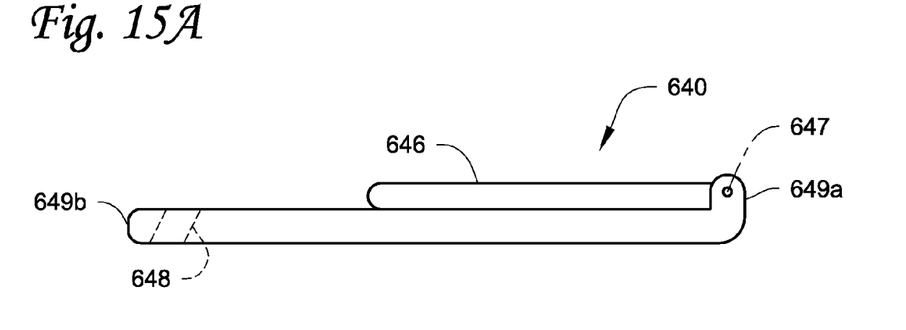
FIG. 15A depicts a backstop that includes a tissue restriction element in a delivery configuration.
Figure 15B:
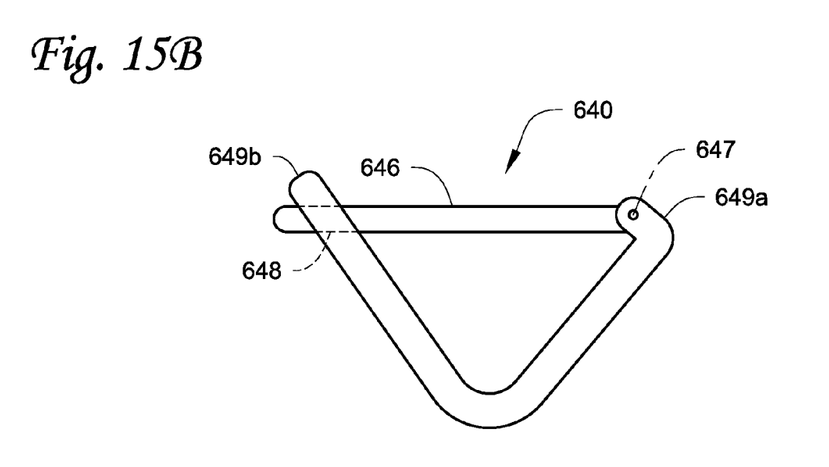
FIG. 15B depicts the backstop of FIG. 15A in a deployed configuration.
Figure 15C:
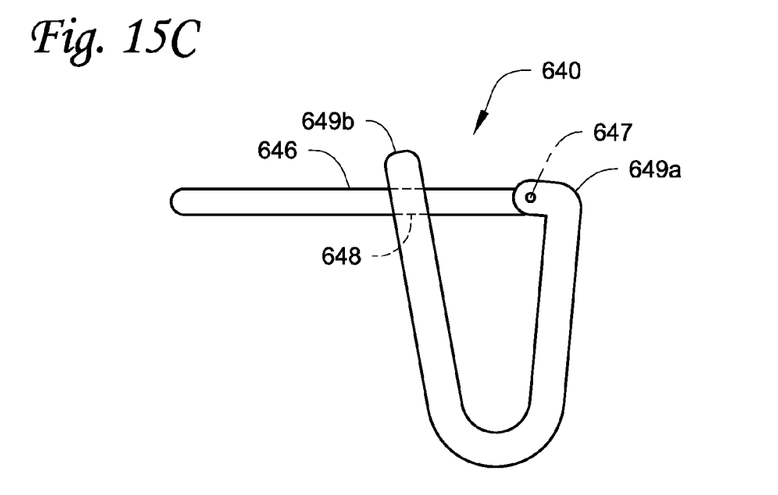
FIG. 15C depicts the backstop of FIG. 15B after actuation of a stapler.

Another embodiment of a backstop that may be used with some embodiments of the surgical stapler delivery systems described herein is depicted in FIGS. 15A-15C. The backstop 640 as depicted in FIG. 15A is in a delivery configuration in which the backstop 640 can be delivered through a lumen in a delivery sheath as described herein. It may be preferred that, in the depicted delivery configuration, the backstop 640 can take on a linear configuration such that the first end 649a and the second end 649b of the backstop 640 are aligned with each other on a line that extends through the backstop 640 itself. The backstop 640 may preferably, after removal from a delivery lumen take on a U- or V-shape as depicted in, e.g., FIG. 15B.

Another feature of the backstop 640 may include, e.g., a tissue restriction element 646 that, in the depicted embodiment is pivotally connected to the backstop 640 proximate the first end 649a. The tissue restriction element 646 may preferably be capable of alignment with the backstop 640 so that the tissue restriction element 646 can be delivered through a delivery lumen along with the backstop 640 as described herein. Although in some embodiments that tissue restriction element 646 may pivot around an axis that is, e.g., defined by a pin or other mechanical element, the tissue restriction element 646 may be bent or otherwise restrained such that it moves to the orientation depicted in FIG. 15B when it is, e.g., not restrained within a delivery lumen.

The backstop 640 may also include an opening 648 proximate the second end 649b such that the tissue restriction element 646 can be supported as it spans the opening between the first end 649a and the second end 649b of the backstop 640. The free end of the tissue restriction element 646 may be directed through the opening 648 as the backstop moves from the linear delivery configuration of FIG. 15A to the curved configuration depicted in FIG. 15B.

In use, the backstop may be attached to the ends of a staple cartridge and an anvil as described herein, i.e., so that the staple cartridge and the anvil face each other across a gap in which the tissue to be stapled is located. Typically, one of the ends 649a and 649b is attached to the staple cartridge and the other end is attached to the anvil. As the staple cartridge and anvil move towards each other to staple tissue (as described herein), the tissue restriction element 646 preferably prevents or limits tissue from entering the gap between the ends 649a and 649b of the backstop 640. Controlling the movement of tissue into that gap can improve the stapling performance by restricting the amount of unstapled tissue (i.e., tissue that could otherwise enter the gap between the ends 649a and 649b of the backstop 640).

In those embodiments in which the staple cartridge and the anvil move towards each other during stapling, the backstop 640 may need to deform or bed into a configuration such as that depicted in FIG. 15C where the ends 649a and 649b of the backstop are closer to each other than in the configuration depicted in FIG. 15B. It may be preferred that the end 649b of the backstop 640 move along the tissue restriction element 646, with the tissue restriction element 646 sliding (in the depicted embodiment) through the opening 648 in the backstop 640.

Figure 16A:
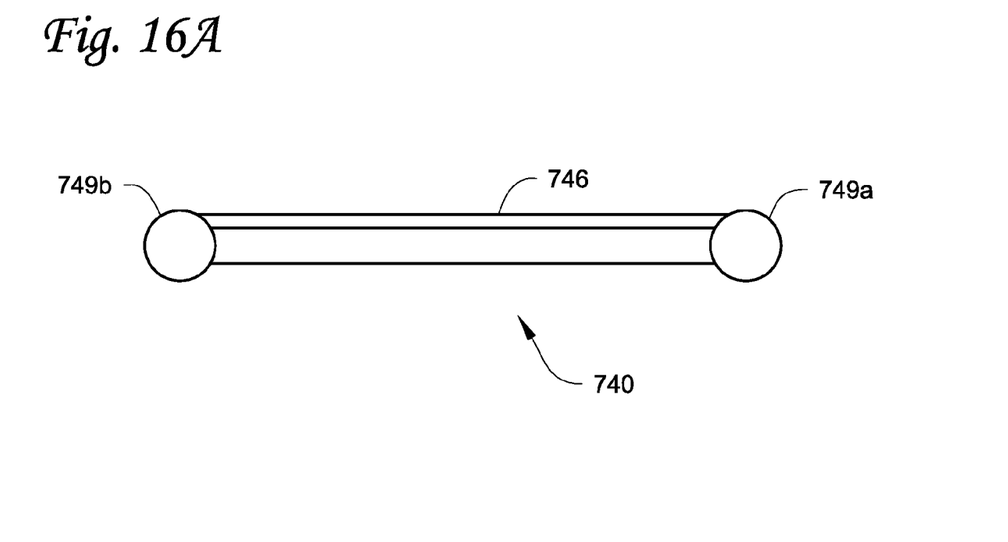
FIG. 16A depicts another backstop that includes a tissue restriction element in a delivery configuration.
Figure 16B:
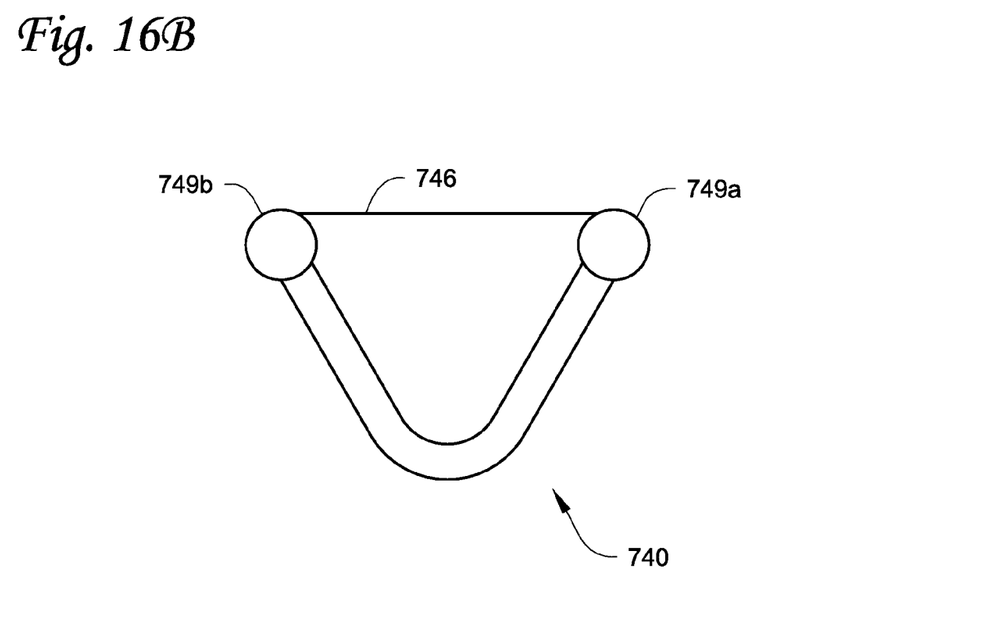
FIG. 16B depicts the backstop of FIG. 16A in a deployed configuration.

Another embodiment of a backstop 740 that includes a tissue restriction element 746 is depicted in FIGS. 16A and 16B. In the embodiment depicted in those figures, the tissue restriction element 746 may be in the form a flexible component that spans the gap between the ends 749a and 749b of the backstop 740. In FIG. 16A, the backstop 740 is in a linear delivery configuration suitable for delivery through a delivery lumen as described herein. The backstop 740 may preferably, after removal from a delivery lumen take on a U- or V-shape as depicted in, e.g., FIG. 16B.

The tissue restriction element 746 may be in the form a line, cable, tape, etc. that can be stretched to take on the longer configuration seen in FIG. 16A and that then shortens to take on the shorter configuration depicted in FIG. 16B. Alternatively, the tissue restriction element 746 may be substantially inextensible and the backstop 740 may include a retraction mechanism in one of both ends 749a and 749b that winds up or otherwise shortens the tissue restriction element 746 as a part of the deployment and stapler assembly process.

Figure 17A:
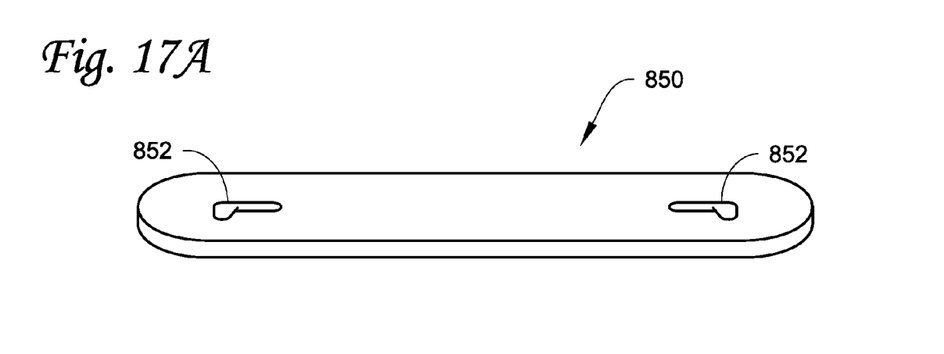
FIG. 17A is a perspective view of another end cap that may be used with some embodiments of the surgical staplers described herein.
Figure 17B:
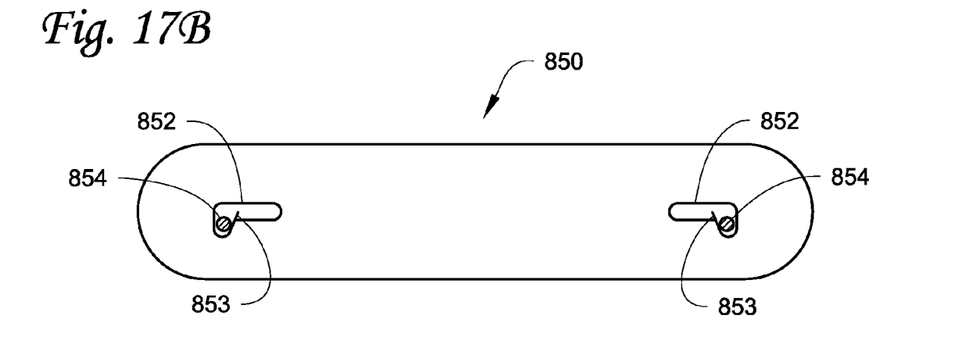
FIG. 17B depicts the end cap of FIG. 17A before actuation of a surgical stapler.
Figure 17C:
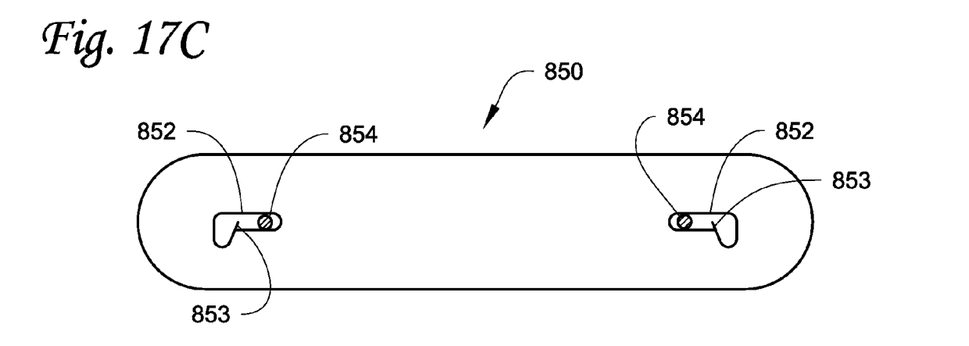
FIG. 17C depicts the end cap of FIG. 17B after actuation of a surgical stapler.

Another embodiment of an end cap 850 that may be used in connection with the surgical staplers described herein as depicted in FIGS. 17A-17C. The end cap 850 may be used to hold a staple cartridge and anvil in a selected arrangement at the opposite end of the surgical stapler from the end at which the backstop is located. The end cap 850 includes two openings 852 that may be used to allow passage of a guidewire that is used in connection with some embodiments of the surgical staplers described herein.

In some embodiments, the openings 852 may be sized to receive mating ends of the staple cartridge and/or anvil to provide additional structural stability to the components of the stapler. Further, one or both of the openings 852 may be in the form of a track to assist in guiding the staple cartridge and/or anvil during the stapling operation. In the depicted embodiment, the openings 852 form paths that require movement in two directions when going from the outboard positions of FIG. 17B to the inboard positions of FIG. 17C.

Referring to FIG. 17B, one or both of the openings 852 may include a retention element or structure 853 that restricts movement of a guidewire or other element in the opening. In particular, it may be preferred that the retention element 853 prevents return of a guidewire, staple cartridge, anvil, etc. after it has moved in one direction (typically inward towards the center of the end cap 850). For example, in FIG. 17B the guidewires 854 in the openings 852 are shown in the outer or outboard position. In FIG. 17C, the guidewires 854 are depicted as being located in an inner or inboard position. Once the guidewire 854 has moved past the retention element 853 in each of the openings 852, the retention element 853 preferably prevents or at least restricts movement back to the outboard position of FIG. 17B. The retention elements 853 may take the form of arms, paddles, etc.

Figure 18:
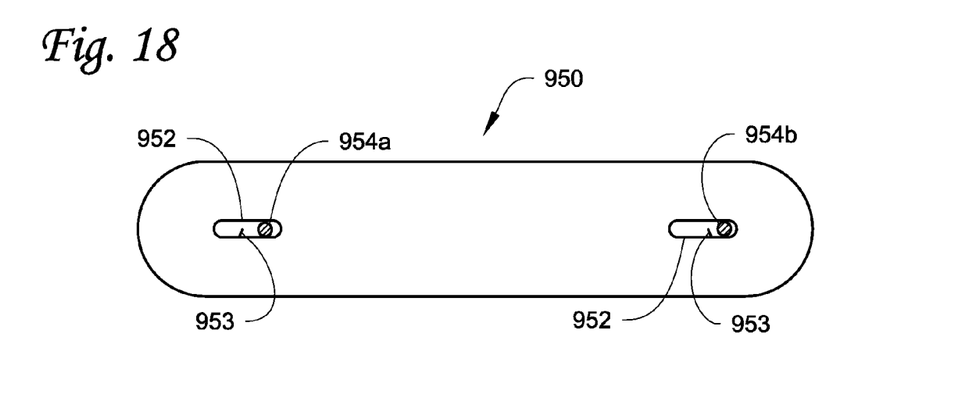
FIG. 18 depicts another embodiment of an end cap that may be used with some embodiments of the surgical staplers described herein.

Another embodiment of an end cap 950 is depicted in FIG. 18. The end cap 950 also includes two openings 952 that, unlike openings 852 in end cap 850, are generally straight, such that movement from the outboard position (see guidewire 954b) to the inboard position (see guidewire 954a) can occur in a substantially linear motion within the openings 952. Each of the openings 952 in the end cap 950 also includes an optional retention element 953 similar to the retention elements 853 described in connection with end cap 850.

Other considerations and/or variations that may be provided in various embodiments of the surgical staplers are described below.

The backstops may be provided as a single piece designed to, e.g., allow easy entrance and passage of a guidewire through a lumen formed therethrough. The backstops could alternatively be provided as multi-component articles that are assembled on site (see, e.g., FIG. 9) with the different portions of the backstop potentially fixed to either the anvil or the staple cartridge. Backstops may also be hinged as described herein. It may be preferred that the backstops define a fixed distance between the anvil and the staple cartridge.

The delivery systems used may include an inner sheath that is delivered through an outer delivery sheath. The inner sheath may, in some embodiments, be similar in structure to a cystoscope and include, e.g., additional channels for the delivery and/or removal of, e.g., other tools, fluids, materials, etc.

In still other embodiments, a single inner sheath may not be used and the outer delivery sheath may be provided with imaging components integrated therein to provide images of the stapler during assembly, use, etc. In such an embodiment, the stapler components may potentially be delivered through component sheaths that may function as conduits for the stapler components, guidewires, imaging equipment, graspers, etc. The distances between the components sheaths may be fixed (by, e.g., passing the sheaths through separate channels, etc.) or variable.

The staple cartridges used in connection with the surgical staplers described herein may potentially include one or more rows of staples arranged to form a staple line when used. In some embodiments, the staple cartridge may include two or more rows of staples arranged on opposing sides of a cutting instrument (e.g., a blade) to allow for simultaneous cutting and stapling. Alternatively, the staple cartridge may only be used for stapling, with no cutting instrument provided therein.

The complete disclosure of the patents, patent documents, and publications cited in the Background, the Description of Illustrative Embodiments, and elsewhere herein are incorporated by reference in their entirety as if each were individually incorporated.

Illustrative embodiments have been discussed and reference has been made to possible variations within the scope of this disclosure. These and other variations and modifications will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:
1. A stapler delivery system comprising:
a backstop comprising a backstop lumen extending through the backstop, the backstop lumen extending between a first opening and a second opening;

an anvil comprising a distal end operably connectable to the backstop;

a staple cartridge comprising a distal end operably connectable to the backstop such that a working surface of the anvil faces a working surface of the staple cartridge;

wherein the staple cartridge comprises a plurality of staples; and wherein the anvil, the backstop, and the staple cartridge are located within a single delivery sheath in a disassembled configuration.

2. The stapler delivery system according to claim 1, wherein the system further comprises a guidewire threaded through at least one of the anvil and the staple cartridge.

3. The stapler delivery system according to claim 1, wherein the backstop comprises a tissue restriction element that spans a gap between the staple cartridge and the anvil when the staple cartridge and the anvil are connected to the backstop.

4. The stapler delivery system according to claim 3, wherein the tissue restriction element is pivotally connected to the backstop such that the tissue restriction element rotates about an axis that extends through the backstop.

5. The stapler delivery system according to claim 3, wherein the tissue restriction element comprises a flexible component that extends between a first end and a second end of the backstop, and wherein the flexible component is held under tension between the first end and the second end.

6. The stapler delivery system according to claim 1, wherein the system further comprises an end cap configured for attachment to the staple cartridge and the anvil.

7. A stapler delivery system comprising:
an anvil comprising a hinged end and a free end;
a staple cartridge comprising a hinged end and a free end;
a hinged backstop rotatably connected to the hinged ends of the staple cartridge and the anvil, wherein, during advancement of the anvil, the staple cartridge and the hinged backstop through a channel in a delivery sheath, the hinged backstop is located between the anvil and the staple cartridge;
wherein rotation of at least one of the anvil and the staple cartridge about the hinged backstop places a working surface of the anvil facing a working surface of the staple cartridge.

8. The stapler delivery system according to claim 7, wherein the hinged backstop defines a first and a second axis of rotation that are spaced apart from each other, and wherein the anvil rotates about the first axis of rotation and the stapler cartridge rotates about the second axis of rotation.

9. The stapler delivery system according to claim 7, wherein the anvil, the hinged backstop, and the staple cartridge are located within a delivery sheath in a disassembled configuration.

10. A method of assembling a stapler comprising:
providing a delivery sheath comprising a proximal end and a distal end;
locating a backstop and the distal end of the delivery sheath proximate each other, the backstop comprising a backstop lumen extending through the backstop, the backstop lumen extending between a first opening and a second opening;
advancing a first end of a guidewire through the delivery sheath towards the distal end of the delivery sheath;
directing the first end of the guidewire through the delivery sheath and into the first opening of the backstop lumen followed by advancing the first end of the guidewire through the backstop lumen until the first end of the guidewire exits the backstop lumen through the second opening;
directing the first end of the guidewire back into the delivery sheath after the first end exits the second opening of the backstop lumen, following by advancing the first end of the guidewire towards the proximal end of the delivery sheath;
advancing an anvil through the delivery sheath towards the distal end of the delivery sheath, wherein advancing the anvil through the delivery sheath comprises advancing the anvil over at least a portion of the guidewire until the anvil exits the delivery sheath proximate the distal end of the delivery sheath;
operably connecting a distal end of the anvil to the backstop after the anvil has exited from the delivery sheath;
advancing a staple cartridge through the delivery sheath towards the distal end of the delivery sheath, wherein advancing the staple cartridge through the delivery sheath comprises advancing the staple cartridge over at least a portion of the guidewire until the staple cartridge exits the delivery sheath proximate the distal end of the delivery sheath, wherein the staple cartridge comprises a plurality of staples and an actuating bead;
operably connecting a distal end of the staple cartridge to the backstop after the staple cartridge has exited from the delivery sheath, wherein the staple cartridge opposes the anvil; and
operably connecting a proximal end of the anvil to a proximal end of the staple cartridge.

11. The method of assembling a stapler according to claim 10, wherein the delivery sheath comprises a delivery lumen that comprises a proximal opening proximate the proximal end of the delivery sheath and a distal opening proximate the distal end of the delivery sheath, and wherein locating the backstop and the distal end of the delivery sheath proximate each other comprises advancing the backstop through the delivery lumen until the backstop exits the delivery lumen from the distal opening.

12. The method of assembling a stapler according to claim 10, wherein the delivery sheath comprises a first guidewire lumen, and wherein directing the first end of the guidewire through the delivery sheath and into the first opening of the backstop lumen comprises advancing the first end of the guidewire through the first guidewire lumen.

13. The method of assembling a stapler according to claim 10, wherein the delivery sheath comprises a second guidewire lumen, and wherein directing the first end of the guidewire back into the delivery sheath after the first end exits the second opening of the backstop lumen and advancing the first end of the guidewire towards the proximal end of the delivery sheath comprises advancing the first end of the guidewire through the second guidewire lumen.

14. The method of assembling a stapler according to claim 10, wherein operably connecting a proximal end of the anvil to a proximal end of the staple cartridge comprises operably connecting an end cap to the proximal ends of the staple cartridge and the anvil.

15. The method of assembling a stapler according to claim 14, wherein the end cap is delivered to a location proximate the staple cartridge and the anvil through the delivery sheath.

16. The method of assembling a stapler according to claim 14, wherein the guidewire is threaded through at least one opening in the end cap.

17. The method of assembling a stapler according to claim 10, further comprising driving a plurality of staples of the plurality of staples from the staple cartridge against the anvil after operably connecting the free end of the anvil to the free end of the staple cartridge.

18. A method of assembling a stapler comprising:
advancing hinged stapler components through a delivery sheath towards a distal end of the delivery sheath, wherein the stapler components comprise an anvil comprising a hinged end and a free end and a staple cartridge comprising a hinged end and a free end, wherein the hinged ends of the staple cartridge and the anvil are rotatably connected to each other through a hinged backstop, wherein the anvil and the staple cartridge are advanced through the delivery sheath in series with each other such that the hinged backstop is located between the anvil and the staple cartridge, and wherein the anvil and the staple cartridge exit the delivery sheath proximate the distal end of the delivery sheath;
rotating at least one of the anvil and the staple cartridge about the hinged backstop after the anvil and the staple cartridge exit the delivery sheath such that a working surface of the anvil faces a working surface of the staple cartridge; and operably connecting the free end of the anvil to the free end of the staple cartridge.

19. The method of assembling a stapler according to claim 18, wherein the hinged backstop defines a first and a second axis of rotation that are spaced apart from each other, and wherein the anvil rotates about the first axis of rotation and the stapler cartridge rotates about the second axis of rotation.

20. The method of assembling a stapler according to claim 18, wherein advancing the hinged stapler components comprises advancing the hinged stapler components over a guidewire.

21. The method of assembling a stapler according to claim 18, wherein the delivery sheath comprises a delivery lumen that comprises a proximal opening proximate the proximal end of the delivery sheath and a distal opening proximate the distal end of the delivery sheath, and wherein advancing hinged stapler components comprises advancing the hinged stapler components through the delivery lumen until both the anvil and the stapler cartridge exit the delivery lumen from the distal opening.

22. The method of assembling a stapler according to claim 18, wherein operably connecting the free end of the anvil to the free end of the staple cartridge comprises operably connecting an end cap to the proximal ends of the staple cartridge and the anvil.

23. The method of assembling a stapler according to claim 22, wherein the end cap is delivered to a location proximate the staple cartridge and the anvil through the delivery sheath.

24. The method of assembling a stapler according to claim 18, further comprising driving a plurality of staples of the plurality of staples from the staple cartridge against the anvil after operably connecting the free end of the anvil to the free end of the staple cartridge.

* * * * *